(12) United States Patent
Carr et al.

(10) Patent No.: US 8,802,890 B2
(45) Date of Patent: Aug. 12, 2014

(54) PROCESS FOR MANUFACTURING ISOCYANATES

(75) Inventors: Robert Henry Carr, Bertem (BE); Johannes Lodewijk Koole, Kessel-Lo (BE); Udo Brian Dave Mike Rodger Bruinsma, Shanghai (CN)

(73) Assignee: Huntsman International LLC, The Woodlands, TX (US)

( * ) Notice: Subject to any disclaimer, the term of this patent is extended or adjusted under 35 U.S.C. 154(b) by 0 days.

(21) Appl. No.: 13/130,773

(22) PCT Filed: Nov. 5, 2009

(86) PCT No.: PCT/EP2009/064703
§ 371 (c)(1),
(2), (4) Date: May 24, 2011

(87) PCT Pub. No.: WO2010/060773
PCT Pub. Date: Jun. 3, 2010

(65) Prior Publication Data
US 2011/0224395 A1 Sep. 15, 2011

(30) Foreign Application Priority Data

Nov. 26, 2008 (EP) ..................... 08170008

(51) Int. Cl.
*C07C 265/12* (2006.01)
*C07C 263/10* (2006.01)

(52) U.S. Cl.
CPC ................... *C07C 263/10* (2013.01)
USPC ........... 560/359; 560/338; 560/341; 560/347; 560/349; 560/358

(58) Field of Classification Search
USPC .................. 560/338, 341, 347, 349, 358, 359
See application file for complete search history.

(56) References Cited

U.S. PATENT DOCUMENTS

| | | | |
|---|---|---|---|
| 3,458,558 A * | 7/1969 | Cheng | 560/353 |
| 4,465,639 A | 8/1984 | Hatfield, Jr. | |
| 4,581,174 A | 4/1986 | Ohlinger et al. | |
| 4,764,308 A * | 8/1988 | Sauer et al. | 562/847 |
| 4,774,357 A | 9/1988 | Keggenhoff et al. | |
| 5,207,942 A | 5/1993 | Scherzer et al. | |
| 5,208,368 A | 5/1993 | Scherzer et al. | |
| 5,312,971 A | 5/1994 | Adkins et al. | |
| 5,364,958 A | 11/1994 | Ishida et al. | |
| 5,386,059 A | 1/1995 | Bolton et al. | |
| 6,140,382 A | 10/2000 | Gallus et al. | |
| 6,229,043 B1 * | 5/2001 | Scherzer et al. | 560/333 |
| 6,395,925 B1 * | 5/2002 | Danielmeier et al. | 560/352 |
| 6,576,788 B1 | 6/2003 | Penzel et al. | |
| 6,900,348 B1 | 5/2005 | Reif et al. | |
| 2004/0024244 A1 * | 2/2004 | Walsdorff et al. | 560/347 |
| 2005/0118088 A1 * | 6/2005 | Olbert et al. | 423/416 |
| 2007/0167646 A1 | 7/2007 | Wershofen et al. | |
| 2007/0269365 A1 * | 11/2007 | Weber et al. | 423/502 |

FOREIGN PATENT DOCUMENTS

| | | | | |
|---|---|---|---|---|
| DE | 19 817 691.0 A | 10/1999 | | |
| EP | 0 133 538 A | 2/1985 | | |
| EP | 0 445 602 A | 9/1991 | | |
| EP | 0 446 781 A | 9/1991 | | |
| EP | 0 467 125 A | 1/1992 | | |
| EP | 0 538 500 A | 4/1993 | | |
| EP | 0 546 398 A | 6/1993 | | |
| EP | 0 561 225 A | 9/1993 | | |
| EP | 0 581 100 A | 2/1994 | | |
| EP | 0 751 118 A | 1/1997 | | |
| EP | 1 890 998 A | 2/2008 | | |
| JP | 10120410 A * | 5/1998 | | C01B 31/28 |

* cited by examiner

*Primary Examiner* — Michael L Leonard
(74) *Attorney, Agent, or Firm* — Robert A. Diaz

(57) ABSTRACT

The present invention relates to a process for manufacturing isocyanates from an amine compound. The process comprises the steps of
  a) Providing chlorine;
  b) Providing carbon monoxide;
  c) Reacting said chlorine and said carbon monoxide for providing phosgene, the carbon monoxide being provided in an adjustable molar excess;
  d) Providing an amine compound and phosgenating said amine compound using said phosgene thereby providing said isocyanate;
the process further comprises adjusting said adjustable molar excess, i.e. the molar excess of carbon monoxide, for adjusting the color of the isocyanate.

9 Claims, No Drawings

PROCESS FOR MANUFACTURING ISOCYANATES

CROSS-REFERENCE TO RELATED APPLICATIONS

This application is the National Phase of International Application PCT/EP2009/064703 filed Nov. 5, 2009 which designated the U.S. and which claims priority to EP App. Serial No. 08170008.0 filed Nov. 26, 2008. The noted applications are incorporated herein by reference.

The present invention relates to light-colored isocyanates, a process for preparing light-colored isocyanates and their use in urethane compounds, in particular in polyurethanes, for example in polyurethane foams.

Isocyanates and isocyanate mixtures are prepared by known methods by phosgenation of the corresponding amines. For polyurethane foams, use is made, for example, of bifunctional or polyfunctional aromatic isocyanates of the diphenylmethane diisocyanate series (MDI). Due to the preparation process, the phosgenation and subsequent work-up (removal of the solvent; separation of monomeric MDI) often results in dark-colored products which in turn give yellowish polyurethane foams or other, likewise discolored PUR materials. This is undesirable, since such discoloration adversely affects the overall visual impression and allows slight inhomogeneities to be observed, e.g. as streaks in the foams obtained. Light-colored isocyanates or isocyanates which contain a reduced amount of color-imparting components are therefore preferred as raw materials.

There have always been many attempts to obtain polyisocyanates, in particular ones of the diphenylmethane diisocyanate series, having a light color. Numerous methods are known for empirically lightening the color of MDI. However, the nature of the troublesome colored substances has hitherto been elucidated only to an unsatisfactory degree.

The previously known methods can be divided into five groups:

1. Processes in which the Starting Amine Material, such as Diaminodiphenylmethane (MDA) or its Oligomers, have been Subjected to Treatment and/or Purification EP-A 0 546 398 describes a process for preparing polymeric MDI in which the polymethylene-polyphenylene-polyamine used as starting material is acidified prior to phosgenation.

EP-A 0 446 781 relates to a process for preparing polymeric MDA (monomeric and oligomeric polymethylene-polyphenylene-polyamines) which are firstly treated with hydrogen and subsequently subjected to a phosgenation, with a relatively light-colored MDI being obtained.

The above mentioned methods give only a slight improvement in the color, since the colored substances in the MDI have been found on the basis of experience to be formed not only from certain MDA secondary components but also to result from color precursors which are formed by secondary reactions during the phosgenation.

2. Process Engineering Solutions in the Phosgenation Process Applied to the Starting Amine Material U.S. Pat. No. 5,364,958 relates to a process for preparing polyisocyanates in which, after the phosgenation, the phosgene is removed completely at low temperature and the isocyanate is subsequently treated hot with HCl gas.

DE 19817691.0 describes a process for preparing MDI/PMDI mixtures having a reduced content of chlorinated by-products and a reduced iodine color number by adherence to defined parameters in the phosgenation reaction. In particular, adherence to particular phosgene/HCl ratios in the reaction step are required here. This process has the disadvantage that a variation of the parameters in the phosgenation is made difficult and the quality of the phosgenation is very sensitive as a result. In addition, the lack of flexibility in the parameters in the phosgenation makes the phosgenation very difficult to carry out in practice and requires a high engineering outlay.

Although processes of the type mentioned attempt to remove discoloring components, they are not efficient enough, both because of their high engineering outlay or the high costs and also in terms of their color-lightening effect, since only slight degradation of color precursors occurs due to incomplete chemical reactions.

EP1890998 describes a process for preparing mixtures comprising diphenylmethane diisocyantes and polyphenylpolymethylene polyisocyanates having a higher Hunter-Lab color (L) number by staged reaction of the corresponding mixtures of diphenylmethanediamines and polyphenylpolymethylenepolyamines with phosgene in the presence of at least one solvent whereby in a first stage the corresponding carbamoyl chlorides and amine hydrochlorides are formed and whereby in a subsequent stage the residual carbamoyl chlorides are dissociated into the corresponding polyisocyanates and hydrogen chloride and amine hydrochlorides are phosgenated to form ultimately the corresponding polyisocyanates in which some amine hydrochlorides remain unreacted at the point where residual excess phosgene is removed from the reaction mixture.

The above-described method has the disadvantage that variation of parameters in the phosgenation can be problematic and the quality of the phosgenation can be sensitive as a result.

3. Addition of Color-lightening Additives to the Crude Isocyanate Product Obtained after the Phosgenation and Before the Work-up.

EP-A 0 581 100 relates to a process for preparing polyisocyanates in which a chemical reducing agent is added after the phosgenation and before the removal of solvent, which according to this document likewise gives light-colored products.

According to U.S. Pat. No. 4,465,639, water is added to the crude product obtained after the phosgenation in order to lighten its color. EP-A 538 500, EP-A 0 445 602 and EP-A 0 467 125 describe the addition of carboxylic acids, alkanols or polyether polyols after the phosgenation for the same purpose.

Although the above-described methods of lightening the color are efficient, they have disadvantages in that the additives not only lighten the color but also undergo reactions with the isocyanates obtained as product, generally resulting, for example, in an undesirable reduction in the isocyanate content. In addition, there is the risk of formation of undesirable by-products in the MDI.

4. After-treatment of the Obtained Isocyanate End Product

EP-A 0 133 538 describes the purification of isocyanates by extraction, giving fractions of a light-colored MDI.

EP-A 0 561 225 describes a process for preparing isocyanates or isocyanate mixtures which, according to this document, contain no color-imparting components, in which process the isocyanates obtained after the phosgenation of the corresponding amines are subjected to a hydrogen treatment at a pressure of from 1 to 150 bar and a temperature of from 100 to 180° C. According to the examples described there, isocyanate end products are hydrogenated as such or in the form of their solutions in suitable solvents.

These color-improving after-treatments of the isocyanate end products after complete removal of the solvent at elevated temperature are likewise not very efficient, since the high temperatures occurring during the work-up, in particular during the distillation of the solvent and (in the case of the preparation of polymeric MDI) the removal of monomeric MDI, have already resulted in the formation of stable colored substances which can be chemically degraded only with difficulty.

5. Control of the Quality of the Phosgene used to Phosgenate the Starting Amine Material The phosgene used to convert amines to the corresponding isocyanates is manufactured conventionally at industrial scale by reaction of chlorine with carbon monoxide in customary and known processes as are described, for example, in Ullmanns Enzyklopädie der industriellen Chemie, $3^{rd}$ Edition, Volume 13, pages 494-500. The phosgene manufacture is carried out typically over one or more generally high purity carbon catalysts which may have been optionally surface- or otherwise treated. In order to avoid feeding free chlorine to the isocyanate manufacturing system which results in significant levels of undesirable by-products, the phosgene is typically manufactured whilst keeping the CO in stoichiometric excess. Unreacted CO may be separated off, optionally purified and subsequently returned to the phosgene plant. Some CO also leaves the plant with the hydrogen chloride gas which is typically then used in one or more further chemical processes. The undesirable by-products which form if free chlorine is fed to the isocyanate manufacturing plant, in particular in the phosgenation process, can be quantified by various analytical methods including determination of total chlorine in the end product for example by X-ray fluorescence spectroscopy.

For example, US20070167646 teaches that it is possible to produce light-colored isocyanates by using phosgene containing less than about 100 ppm, preferably less than about 60 ppm, more preferably less than about 20 ppm of sulfur in elemental or bound form in the production of the isocyanates. The range statement "less than about 100 ppm of sulfur" means that less than about 100 ppm of sulfur, based on the weight of phosgene used, is contained in the phosgene used. The sulfur content in the phosgene substantially results from the carbon monoxide (CO) used to produce the phosgene, which contains a certain proportion of sulfur depending on its origin. The sulfur content again results predominantly from the sulfur content of the raw materials used to produce the CO. The phosgene with a low sulfur content used in the process according to the invention can be produced by various methods known to the person skilled in the art. One way of guaranteeing a low sulfur content in phosgene is, for example, the use of starting compounds in phosgene production that already have a correspondingly low sulfur content. In particular, the use of CO with a correspondingly low sulfur content is suitable here. Processes for the production of CO with a low sulfur content are known to those skilled in the art. Thus, for example, it is possible to use CO obtained by coal gasification, steam reforming, $CO_2$ reforming, partial oxidation of hydrocarbons or other processes. CO can also be obtained by separation from gas mixtures containing CO. Processes of this type for the production or obtaining of CO are described e.g. in Chemische Technik (editors: Dittmeyer, Keim, Kreysa, Oberholz), 5.sup.th edition, Vol. 4, pages 981-1007.

Further teaching on the stringent requirements for phosgene quality is given for example in U.S. Pat. No. 6,900,348 which describes a process for preparing light colored isocyanates by reacting an amine or a mixture of two or more amines with phosgene containing less than 50 ppm of bromine or iodine or their mixtures in molecular or bound form. US20040024244 teaches that the chlorine with low bromine content to be used for the production of light colored isocyanates may be generated by oxidizing the hydrogen chloride produced in the isocyanate production process.

Chlorine is produced industrially from rock salt, sea salt or mined potassium chloride. Here, chlorine is usually produced together with sodium or sodium hydroxide as coproduct by electrolysis of a rock salt solution. Potassium chloride is used analogously for the production of chlorine together with potassium or potassium hydroxide. The salts used in the electrolysis usually contain bromine and iodine compounds in amounts of from 30 to 3000 ppm and these form bromine or iodine during the electrolysis. A disadvantage of the above-described process is the high cost of purification required to reduce the bromine and iodine content in the chlorine used for the phosgene synthesis to such an extent that the resulting phosgene to be used in isocyanate production has the necessary low content of bromine, iodine, bromine-containing or iodine-containing compounds. Major disadvantages of making high purity chlorine by converting the hydrogen chloride produced in the isocyanate production process are the requirement for extensive additional high capital cost process equipment and the high electricity costs.

There remains a need for a process for the manufacture of light colored isocyanates by reacting amines with phosgene where the phosgene is produced using chlorine which may contain bromine in the range 50 to 500 ppm in molecular or bound form. It is further an object of the present invention to provide light colored isocyanates using a method that avoids at least to some extent the disadvantages or drawbacks of the methods of prior art as set out above.

It is an object of the present invention to provide a process for the manufacture of light colored isocyanates, especially those of the PMDI series, by phosgenation of the corresponding amine using phosgene produced from chlorine, which chlorine may contain bromine in the range 50 to 500 ppm in molecular or bound form.

It is an object of the present invention to provide a process for the manufacture of isocyanate, in which the colour of the isocyanate can be controlled, adjusted, changed to a lighter or darker colour and/or kept within acceptable ranges.

One or more of the above objectives are accomplished by a process for providing isocyanate according to the present invention.

We have surprisingly found that this need can be satisfied by manufacturing the phosgene under conditions of careful control of the amount of excess CO present in the process.

According to a first aspect of the present invention, a process for manufacturing isocyanates from an amine compound is provided. The process comprises the steps of
   a) Providing chlorine;
   b) Providing carbon monoxide;
   c) Reacting said chlorine and said carbon monoxide for providing phosgene, the carbon monoxide being provided in an adjustable molar excess;
   d) Providing an amine compound and phosgenating said amine compound using said phosgene thereby providing said isocyanate;
the process further comprises adjusting said adjustable molar excess, i.e. the molar excess of carbon monoxide, for adjusting the colour of the isocyanate.

Unless otherwise indicated, "molar excess of carbon monoxide" means the molar excess of carbon monoxide over chlorine in the reactor providing phosgene.

The molar excess of carbon monoxide can be expressed as the mol ratio carbon monoxide over chlorine. A molar excess means a mol ratio being more than, i.e. above, 1:1.

The precise boundaries for the molar excess or mol ratio of carbon monoxide over chlorine, between which adjustment results in varying the colour of the isocyanate, within acceptable ranges, is also function of the physical properties and condition of the reactors (including the one or more catalysts) and instruments used in the process of both providing phosgene and phosgenation of the amine.

An applicable range for the extant mol ratio carbon monoxide over chlorine according to the invention may be less than or equal to 1.025:1.000, i.e. above 1.000:1.000 up to or equal to 1.025:1.000 (i.e. a carbon monoxide excess of more than 0 mol % up to or equal to 2.5 mol %, such as from 0.00001 mol % to 2.5 mol %), such as above 1.000:1.000 up to or equal to 1.020:1.000 (i.e. a carbon monoxide excess of above 0 mol % up to or equal to 2.0 mol %), e.g. above 1.000:1.000 up to 1.015:1.000 (i.e. a carbon monoxide excess of above 0 mol % up to or equal to 1.5 mol %), as an example even the range of above 1.000:1.000 up to or equal to 1.010:1.000 (i.e. a carbon monoxide excess of above 0 mol % up to or equal to 1.0 mol %).

It is in general known to run phosgene production using carbon monoxide excess for producing phosgene to be use to phosgenate amines into corresponding isocyanates. Typical mol ratio carbon monoxide over chlorine are 1.030:1.000 to 1.100:1.000 (i.e. 3 mol % to 10 mol %) for providing phosgene to phosgenate amine compounds into isocyanates, as described in U.S. Pat. No. 4,764,308. Using chlorine excess results in chlorine being present in the phosgene, which, when used as such for phosgenation, results in the provision of chlorine-comprising isocyanate compounds and other chlorine-comprising non-isocyanate compounds for example the product of the reaction of the phosgenation solvent with chlorine, which negatively influence the performance and properties of the isocyanate when used to provide e.g. polyurethane such as polyurethane foam and/or which require provisional additional process equipment in order to remove them from the isocyanate process or product. Hence the presence of chlorine in the phosgene is to be prevented.

According to the present invention, it was surprisingly found that by adjusting the extant molar excess or mol ratio carbon monoxide over chlorine, as present in the process step c) slightly above stochiometrical, in particular in the range of lower molar ratios such above 1.000:1.000 up to or equal to 1.025:1.000 (i.e. a carbon monoxide excess of more than 0 mol % up to or equal to 2.5 mol %, such as from 0.00001 mol % to 2.5 mol %), such as above 1.000:1.000 up to or equal to 1.020:1.000 (i.e. a carbon monoxide excess of above 0 mol % up to or equal to 2.0 mol %), e.g. above 1.000:1.000 up to 1.015:1.000 (i.e. a carbon monoxide excess of above 0 mol % up to or equal to 1.5 mol %), as an example even the range of above 1.000:1.000 up to or equal to 1.010:1.000 (i.e. a carbon monoxide excess of above 0 mol % up to or equal to 1.0 mol %), the colour of the isocyanate obtained using the phosgene provided in step d) can be influenced, i.e. controlled, adjusted to and/or kept at the desired value. This in particular is the case if the chlorine used comprises significant amounts of bromine, such as in the range of 30 ppm to 500 ppm, e.g. in the range of 50 to 500 ppm.

Hence, according to some embodiments of the present invention, the chlorine used in the process may comprise bromine in the range 30 to 500 ppm, e.g. in the range 50 to 500 ppm in molecular or bound form.

The advantage is that no purification of bromine from standard chlorine gas is required, while still being able to obtain acceptable colour grades for the resulting isocyanate.

According to some embodiments of the present invention, the adjusting said adjustable molar excess may comprise defining a target molar excess of said carbon monoxide based upon a required colour of the isocyanate to be obtained and controlling and adjusting the provision of chlorine and carbon monoxide for bringing the extant molar excess of said carbon monoxide to approximate and optionally match said target molar excess.

Adopting the colour of the isocyanate by adjusting said adjustable molar excess may be done by Defining a target molar excess of said carbon monoxide based upon a required colour of the isocyanate to be obtained and Controlling and adjusting the provision of chlorine and carbon monoxide for bringing the extant molar excess of said carbon monoxide in step c) to approximate and optionally match said target molar excess.

The molar excess of carbon monoxide being adjustable means that the extant molar excess, e.g. by means of measuring the mol ratio carbon monoxide over chlorine, can be controlled and adjusted during operation of the process according to the invention. The adjustment of the extant molar excess or the mol ratio carbon monoxide over chlorine may e.g. be done by changing the volume of carbon monoxide provided, changing the volume of chlorine provided, or both.

Means for controlling the process by use of on-line analysers for carbon monoxide and halogens (where halogens includes molecular chlorine or molecular bromine or molecular bromochlorine and the like) or on-line or off-line determination of total chlorine or total bromine in the isocyanate, such as e.g. the resulting PMDI product, may be applied. Controlling the process may include calculating the amount or content of carbon monoxide and/or the amount of content of chlorine in various fluid streams, and calculating the ratio of carbon monoxide and chlorine, based upon calculated or measured values of process parameters and settings, which parameters and/or settings are provided from the process to manufacture the isocyanate.

Both the chlorine and the carbon monoxide may be provided as fresh raw streams of material, or may be partially provided as recycled material. Recycled carbon monoxide may be obtained from purifying the phosgene obtained after process step c) and/or purifying of the isocyanate obtained by process step d). Recycled chlorine may be obtained from the HCl formed in the phosgenation process step. Purifying phosgene or isocyanate may be done using processes well known to the skilled person.

It is clear that adjustments of flows of raw material or optionally streams of recycled materials may be done in any known way which is well known in the art of conducting chemical processes, e.g. by manual interventions, e.g. for adjustment of appropriate valve settings, or by adjusting flows in a controlled way by means of control software in combination with automated valves controlled by said control software.

Optionally, controlling and adjusting the extant molar excess of carbon monoxide may comprise:
 defining or setting a target value for the molar excess or the mol ratio carbon monoxide over chlorine based upon the colour of the isocyanate intended to be produced;
 obtaining information, such as real time information, on the extant molar excess or mol ratio carbon monoxide over chlorine as present in the process; and
 adjusting the extant molar excess or the mol ratio carbon monoxide over chlorine for approximating the extant molar excess or the mol ratio carbon monoxide over chlorine to the target molar excess or the mol ratio carbon monoxide over chlorine.

Optionally, the controlling and adjusting of the molar excess of carbon monoxide may comprise or may further comprise redefining or changing the target value for the molar excess or the mol ratio carbon monoxide over chlorine based upon changed colour requirements of the isocyanate intended to be produced, and/or based upon changed process conditions in steps c) and/or d), and/or based upon changed properties of the raw or optionally recycled materials used in the processes. These raw and/or recycled materials used in the processes may be e.g. the carbon monoxide, chlorine, amine compound(s), as well as products optionally used in the process, e.g. additives or solvents.

According to some embodiments of the present invention, the amine compound may comprise diaminodiphenylmethane.

Diaminodiphenylmethane may also be referred to as DADPM or MDA. The amine compound may even substantially consist of a mixture of isomers of diaminodiphenylmethane, such as 4,4'-MDA, 2,4'-MDA in combination with higher oligomers or homologues of MDA.

Phosgenation of a base product comprising diaminodiphenylmethane, i.e. isomers or homologues of MDA, results in a polyisocyanate mixture comprising methylene diphenyl diisocyanate (MDI), typically a mixture of isomers of MDI, e.g. such as 4,4'-MDI, 2,4'-MDI, and homologues of MDI or oligomeric polyisocyanates. This resulting polyisocyanate mixture is often referred to as polymeric MDI, or PMDI.

The advantage of these embodiments is that the colour of the PMDI can be controlled and kept within acceptable colour grades, which grades are determined by the end use of the isocyanate.

This careful control of CO to chlorine ratio in the manufacture of phosgene for the production of isocyanates, such as TDI and other isocyanates, such as non MDI-isocyanates, can also be beneficial in terms of favorable effects on impurity formation, whether these impact on final product color or on impurities in the products or on process efficiency or the like.

According to some embodiments of the present invention, the amine compound may comprise toluene diamines (in the form of individual substantially pure isomers or mixtures of isomers).

The colour of the produced isocyanate may be characterized by using in-line or off-line techniques. The measured colour can be quoted in terms of the various "colour space" systems such as Hunterlab Lab and CIE L*a*b* and can be determined either on the original isocyanate material or on a solution of the isocyanate in a suitable solvent. Quoting isocyanate colour in the CIE L*a*b* colour space or system, the isocyanate as provided by the process, i.e. not brought in solution, may have a colour grade/value of L* greater than 30, preferably greater than 35, more preferred greater than 40, still preferably greater than 45. In the CIE L*a*b* colour space, the colour grade or value of L* is necessarily less than or equal to 100. Obtained colour grades or values of L* in the CIE L*a*b* colour space for the isocyanates obtainable, are typically less than or equal to 80, such as less than or equal to 60.

According to some embodiments of the present invention, the colour of the isocyanate obtained by the process according to the present invention may have a CIE colour grade/value L* larger than 30.

Changes in a* or b* parameters of the CIE colour space determined on the isocyanate product may also arise as a result of the present invention and may be beneficial in some applications.

For measuring colour grades in HunterLab colour space or the CIE L*a*b* colour space, typically HunterLab test equipment is used, as is well known in the art.

It was noticed that by carefully adjusting the carbon monoxide excess according to the invention, in particular in case of a carbon monoxide over chlorine ratio being in the range above 1.000:1.000 up to or equal to 1.025:1.000 (i.e. a carbon monoxide excess of more than 0 mol % up to or equal to 2.5 mol %, such as from 0.00001 mol % to 2.5 mol %), such as above 1.000:1.000 up to or equal to 1.020:1.000 (i.e. a carbon monoxide excess of above 0 mol % up to or equal to 2.0 mol %), e.g. above 1.000:1.000 up to 1.015:1.000 (i.e. a carbon monoxide excess of above 0 mol % up to or equal to 1.5 mol %), as an example even the range of above 1.000:1.000 up to or equal to 1.010:1.000 (i.e. a carbon monoxide excess of above 0 mol % up to or equal to 1.0 mol %), a significant part of the bromine present in the chlorine before provision of the phosgene, ends up in the isocyanate as bromine bound to the isocyanate or any of the species in the isocyanate provided. This is in particular true when run using chlorine comprising higher amounts of bromine, such as 50 ppm to 500 ppm being present in the chlorine.

When the production of phosgene is run with high excesses of carbon monoxide, less bromine in bound form is noticed in the isocyanate.

According to some embodiments of the process of the present invention, the isocyanate obtained may comprise 30 to 500 ppm of bromine in bound form, such as 30 to 150 ppm of bromine in bound form, e.g. 50 to 150 ppm bromine in bound form.

Hence, according to a further aspect of the present invention, an isocyanate obtained by a process according to the first aspect of the present invention is provided.

An isocyanate according to the second aspect of the present invention may comprise 30 to 500 ppm of bromine in bound form, such as 30 to 150 ppm of bromine in bound form, e.g. 50 to 150 ppm bromine in bound form.

According to some embodiments, the isocyanate may have a colour having a CIE colour grade/value L* larger than 30.

According to a further aspect of the present invention, an isocyanate obtained by a process according to the first aspect of the present invention may be used for providing polyurethane, such as e.g. rigid of flexible polyurethane foam, polyurethane coatings, adhesives and alike.

The result obtained according to the present invention was particularly surprising because it had hitherto not been recognized that such variation of the CO excess used for the manufacture of phosgene used for the preparation of isocyanates is sufficient to influence the product color in a desirable way.

The colour, being a quality aspect of the isocyanate, e.g. PMDI, may be determined by means of adjustment of the CO excess over the chlorine being used in the phosgene manufacture.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrate, by way of example, the principles of the invention. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art from this disclosure.

The following terms are provided solely to aid in the understanding of the invention.

The term "bromine in molecular form" means molecules which consist entirely of bromine atoms. The term "bromine in bound form" means molecules which comprise not only bromine but also atoms different from the specified atoms.

Unless otherwise specified, the term "ppm" means weight parts per million weight parts.

The preparation of isocyanate taking place in the process of the present invention is carried out using a reaction scheme and sequence known to those skilled in the art, i.e. by reacting an amine or a mixture of two or more amines with a superstoichiometric amount of phosgene. It is in principle possible to employ all methods in which a primary amine or a mixture of two or more primary amines is reacted with phosgene to form one or more isocyanate groups.

The phosgene is prepared by reaction of carbon monoxide [CO] and chlorine [$Cl_2$] over one or more carbon catalysts in one or more reactors which can be operated in series or in parallel or in any combination. Different catalysts can be used simultaneously in different reactors. Unreacted CO remaining in the produced phosgene can be separated, optionally purified to the required degree, and recycled to the phosgene plant.

The provision of phosgene from carbon monoxide and chlorine can be done using a single stage reaction or a multistage reaction using subsequent reactors for converting carbon monoxide and chlorine into phosgene.

In case a multistage reaction is carried out for providing phosgene, i.e. using more than one reactor in sequence for reacting carbon monoxide and chlorine into phosgene, adopting the colour of the isocyanate may be done by adjusting the ratio of carbon monoxide over chlorine at least in the reactors where carbon monoxide is in excess, such as at least in the last reactor of the sequence of reactors for producing phosgene.

This is in particular the case if chlorine and/or carbon monoxide is added in the product stream flowing from one of the reactors to the subsequent reactor, e.g. the last reactor.

Some of the reactors may be run using a sub-stochiometrical amount of carbon monoxide. In the reactors run with carbon monoxide excess, adjusting the extant molar excess or mol ratio carbon monoxide over chlorine slightly above stochiometrical, in particular in the range of lower molar ratios such as in the range of above 1.000:1.000 up to or equal to 1.025:1.000 (i.e. a carbon monoxide excess of more than 0 mol % up to or equal to 2.5 mol %, such as from 0.00001 mol % to 2.5 mol %), such as above 1.000:1.000 up to or equal to 1.020:1.000 (i.e. a carbon monoxide excess of above 0 mol % up to or equal to 2.0 mol %), e.g. above 1.000:1.000 up to 1.015:1.000 (i.e. a carbon monoxide excess of above 0 mol % up to or equal to 1.5 mol %), as an example even the range of above 1.000:1.000 up to or equal to 1.010:1.000 (i.e. a carbon monoxide excess of above 0 mol % up to or equal to 1.0 mol %) enables to adjust or control the colour of the isocyanate obtained using the phosgene provided.

Alternatively, no additional carbon monoxide or chlorine is added between subsequent reactors in a multistage reaction. Hence adopting the colour of the isocyanate may be done by adjusting the molar excess in the first reactor of the sequence of reactors for producing phosgene.

In a further step, the phosgene is reacted with at least one amine compound (i.e. phosgenation of an amine), providing an isocyanate.

After phosgenation of the amine, some CO also may leave the plant with the hydrogen chloride gas which is typically then used in one or more further chemical processes ("exported"). The compositions of the carbon monoxide, optionally both the fresh carbon monoxide and the carbon monoxide recycled from after production of the phosgene, chlorine, phosgene, export-HCl and recycle gas streams can be monitored by means of on-line analytical techniques such as gas chromatography, mass spectrometry or spectroscopic techniques (UV-Vis, IR, NIR, etc).

Control of the operation of the phosgene plant, i.e. the production of phosgene, and the subsequent production of isocyanate by phosgenation of a corresponding amine, in terms of achieving the desired ratios of feed gas streams, can be carried out by manual intervention or by means of control software and corresponding valving systems, and can optionally include inputs based on isocyanate product composition, such as MDI product composition, as well as on composition and/or volume of one or more of the various gas streams.

In an embodiment of the invention, the process of the present invention, i.e. the reaction of the amine or the mixture of two or more amines with the phosgene, is carried out in a solvent or a mixture of two or more solvents.

As solvent, it is possible to use all solvents suitable for the preparation of isocyanates. These are preferably inert aromatic, aliphatic or alicyclic hydrocarbons or their halogenated derivatives. Examples of such solvents are aromatic compounds such as monochlorobenzene (MCB) or dichlorobenzene, for example o-dichlorobenzene, toluene, xylenes, naphthalene derivatives such as tetralin or decalin, alkanes having from about 5 to about 12 carbon atoms, e.g. hexane, heptane, octane, nonane or decane, cycloalkanes such as cyclohexane, inert esters and inert ethers such as ethyl acetate or butyl acetate, tetrahydrofuran, dioxane or diphenyl ether.

As amines, it is in principle possible to use all primary amines which can react appropriately with phosgene to give isocyanates. Suitable amines are, in principle, all linear or branched, saturated or unsaturated aliphatic or cycloaliphatic or aromatic primary monoamines or polyamines, provided that these can be converted into isocyanates by means of phosgene. Examples of suitable amines are 1,3-propylenediamine, 1,4-butylenediamine, 1,5-pentamethylenediamine, 1,6-hexamethylenediamine and the corresponding higher homologues of this series, isophoronediamine (IPDA), cyclohexyldiamine, cyclohexylamine, aniline, phenylenediamine, p-toluidine, 1,5-naphthylenediamine, 2,4- or 2,6-toluenediamine or a mixture thereof, 4,4'-, 2,4'- or 2,2'-diphenylmethanediamine or mixtures thereof and also higher molecular weight isomeric, oligomeric or polymeric derivatives of the abovementioned amines and polyamines. In a preferred embodiment of the present invention, the amine used is an amine of the diphenylmethanediamine series or a mixture of two or more such amines.

After going through the process of the present invention, the abovementioned compounds are in the form of the corresponding isocyanates, e.g. as hexamethylene 1,6-diisocyanate, isophorone diisocyanate, cyclohexyl isocyanate, cyclohexyl diisocyanate, phenyl isocyanate, phenylene diisocyanate, 4-tolyl isocyanate, naphthylene 1,5-diisocyanate, tolylene 2,4- or 2,6-diisocyanate or mixtures thereof, diphenylmethane 4,4'-, 2,4'- or 2,2'-diisocyanate or mixtures of two or more thereof, or else higher molecular weight oligomeric or polymeric derivatives of the abovementioned isocyanates or as mixtures of two or more of the abovementioned isocyanates or isocyanate mixtures.

In a preferred embodiment of the present invention, the amines used are the isomeric, primary diphenylmethane-diamines (MDA) or their oligomeric or polymeric derivatives, i.e. the amines of the diphenylmethanediamine series. Diphenylmethanediamine, its oligomers or polymers are obtained, for example, by condensation of aniline with formaldehyde. Such oligoamines or polyamines or mixtures thereof are also used in a preferred embodiment of the invention.

The reaction of the phosgene prepared according to the present invention and which is to be used for the purposes of the present invention with one of the abovementioned amines or a mixture of two or more such amines can be carried out continuously or batchwise in one or more stages. If a single-stage reaction is carried out, this reaction preferably takes place at from about 60 to 200° C., for example at from about 130 to 180° C.

The phosgenation reaction can, for example, be carried out in two stages. Here, in a first stage, the reaction of the phosgene with the amine or the mixture of two or more amines is carried out at from about 0 to about 130° C., for example from about 20 to about 110° C. or from about 40 to about 70° C., with a time of from about 1 minute to about 2 hours being allowed for the reaction between amine and phosgene. Subsequently, in a second stage, the temperature is increased to from about 60 to about 190° C., in particular from about 70 to 170° C., over a period of, for example, from about 1 minute to about 5 hours, preferably over a period of from about 1 minute to about 3 hours.

In a preferred embodiment of the invention, the reaction is carried out in two stages.

During the phosgenation reaction, superatmospheric pressure can, in a further preferred embodiment of the invention, be applied, for example up to about 100 bar or less, preferably from about 1 bar to about 50 bar or from about 2 bar to about 25 bar or from about 3 bar to about 12 bar. However, the reaction can also be carried out under atmospheric pressure or at a pressure below ambient pressure.

Excess phosgene is preferably removed at from about 50 to 180° C. after the reaction. The removal of remaining traces of solvent is preferably carried out under reduced pressure, for example the pressure should be about 500 mbar or less, preferably less than 100 mbar. In general, the various components are separated off in the order of their boiling points; it is also possible to separate off mixtures of various components in a single process step.

The present invention further provides light-colored isocyanates as can be prepared by the process of the present invention. As well as all the analytical methods typically applied to the characterisation of isocyanates which are well known to those skilled in the art, the light colored isocyanates which are produced by the present invention can be further characterised by determination of total chlorine content (for example by X-ray fluoresence), total bromine content (for example by X-ray fluoresence) and colour (for example Hunterlab Lab or CiE L*a*b* values).

The invention further provides for the use of isocyanates, which can be prepared by the process of the present invention, for preparing urethane compounds, in particular polyurethanes. In a preferred embodiment of the invention, the isocyanates of the invention are used for producing polyurethane foams such as, for example, rigid foams, semirigid foams, integral foams and flexible foams.

The invention is illustrated by the following examples.

COMPARATIVE EXAMPLE 1 AND 2

In comparative example 1, an industrial process, chlorine gas containing about 100 ppm of bromine (in unspecified form) and gaseous CO were fed to a phosgene reactor containing a carbon catalyst such that the molar excess of CO to chlorine was 17.10 mol %, i.e. a molar ratio carbon monoxide over chlorine of 1.171:1.000. The reactor is a tube-shell reactor, in which the tubes are filled with catalyst, the shell side being provided with a cooling fluid to evacuate the thermal energy obtained by reacting chlorine and carbon monoxide over the catalyst in the tube. The resulting phosgene was liquefied, mixed with MCB and reacted with a solution of crude polymeric MDA in MCB in a cascade of stirred vessels to form the isocyanate. The mixture leaving the phosgenation was freed of phosgene and monochlorobenzene and after-treated thermally according to the prior art. The L* color (in the CIE L*a*b* colour space) of the MDI produced was 24.7. This molar excess of CO to chlorine of 17.1 mol % was set as target value, whereas the extant mol ratio or molar excess varied within normally accepted ranges as applicable in industrial processes.

For comparative example 2, the volumes of chlorine gas containing about 100 ppm of bromine (in unspecified form) and gaseous carbon monoxide, which gasses were provided to the same reactor as used for comparative example 1, were changed such that the molar excess of CO to chlorine was 5 mol %, i.e. a molar ratio carbon monoxide over chlorine of 1.050:1.000. The resulting phosgene was liquefied, mixed with MCB and reacted with a solution of crude polymeric MDA in MCB in a cascade of stirred vessels to form the isocyanate. The mixture leaving the phosgenation was freed of phosgene and monochlorobenzene and after-treated thermally according to the prior art. The L* color (in the CIE L*a*b* colour space) of the MDI produced was 24.2. This molar excess of CO to chlorine of 5 mol % was set as target value, whereas during the production run deviation of the extant molar excess within generally acceptable ranges was noticed.

As is clear, the adjustment or variation of the carbon monoxide/chlorine molar ratio from 1.171:1.000 to 1.050:1.000 has only a minor significant influence on the colour of the MDI obtained. Merely 0.5 points difference for the L* value (in the CIE L*a*b* colour space) for an increase of about 12 mol % of the carbon monoxide excess is obtained. Adjustment of the ratio in this range hence cannot be used to adjust or control the colour of the MDI produced.

EXAMPLE 1 TO 7

In example 1 according to the invention, in the same industrial process and using the same reactors, chlorine gas containing about 100 ppm of bromine (in unspecified form) and gaseous CO were fed to a phosgene reactor containing a carbon catalyst such that the molar excess of CO to chlorine was 0.4 mol %. The resulting phosgene was liquified, mixed with MCB and reacted with a solution of crude polymeric MDA in MCB in a cascade of stirred vessels to form the isocyanate. The mixture leaving the phosgenation was freed of phosgene and monochlorobenzene and after-treated thermally according to the prior art. The L* color (in the CIE L*a*b* colour space) of the MDI produced was 42.9.

In order to run the process according to a second example, in the same industrial process, the volumes of chlorine gas containing about 100 ppm of bromine (in unspecified form) and gaseous carbon monoxide, which gas streams were fed to a phosgene reactor containing a carbon catalyst, were changed such that the molar excess of CO to chlorine was 0.8 mol %. The resulting phosgene was liquefied, mixed with MCB and reacted with a solution of crude polymeric MDA in MCB in a cascade of stirred vessels to form the isocyanate. The mixture leaving the phosgenation was freed of phosgene and monochlorobenzene and after-treated thermally according to the prior art. The L* color (in the CIE L*a*b* colour space) of the MDI produced was 41.1.

The same industrial process was run using various settings for the carbon monoxide over chlorine ratio, as is further set out in the examples 3 to 7 of table 1.

TABLE 1

| example | carbon monoxide excess (mol %) | Molar ratio carbon monoxide over chlorine (–) | L* in the CIE L*a*b* colour space (–) |
| --- | --- | --- | --- |
| Comparative example 1 | 17.1 | 1.171:1.000 | 24.7 |
| Comparative example 2 | 5.0 | 1.050:1.000 | 24.2 |
| Example 1 | 0.4 | 1.004:1.000 | 42.9 |
| Example 2 | 0.8 | 1.008:1.000 | 41.1 |
| Example 3 | 0.1 | 1.001:1.000 | 52.0 |
| Example 4 | 0.0* | 1.000:1.000* | 50.4 |
| Example 5 | 0.2 | 1.002:1.000 | 54.7 |
| Example 6 | 0.4 | 1.004:1.000 | 47.0 |
| Example 7 | 0.3 | 1.003:1.000 | 49.0 |

*carbon monoxide present in amount slighty above stochiometric

As is clear from table 1, in case the carbon monoxide excess is kept low, such as in the range of 0 mol % to 2.5 mol %, such as in the range of 0 mol % to 2.0 mol %), preferably in the range of 0 mol % to 1.5 mol %, more preferred in the range of 0 mol % to 1.0 mol %, minor adjustments of the carbon monoxide excess enables adjustment or control of the colour of the isocyanate obtained using the phosgene provided. Via adjustment of the carbon monoxide excess, the colour deviations or variations occurring in the process due to other factors, may be compensated at least to some extent.

Comparison of the results between the Comparative Examples and Examples demonstrates a good lightening of the color of crude MDI when using phosgene prepared from CO and chlorine containing about 100 ppm bromine by careful control of the excess CO. It was noticed that the colour of the isocyanate can be improved and kept under control.

It is to be understood that although preferred embodiments and/or materials have been discussed for providing embodiments according to the present invention, various modifications or changes may be made without departing from the scope and spirit of this invention.

The invention claimed is:

1. A process for manufacturing isocyanates from an amine compound, the process comprising the steps of
   a) providing chlorine, wherein the chlorine comprises bromine in the range of 50 to 500 ppm in molecular or bound form;
   b) providing carbon monoxide;
   c) reacting said chlorine and said carbon monoxide for providing phosgene, the carbon monoxide being provided in an adjustable molar excess, wherein the mol ratio of carbon monoxide over chlorine is in a range of above 1.000:1.000 up to or equal to 1.025:1.000;
   d) providing an amine compound and phosgenating said amine compound using said phosgene thereby providing said isocyanate; and
   wherein the process further comprises adjusting said adjustable molar excess for adjusting the colour of the isocyanate.

2. The process according to claim 1, wherein adjusting said molar excess comprises
   defining a target molar excess of said carbon monoxide based upon a required colour of the isocyanate to be obtained; and
   controlling and adjusting the provision of chlorine and carbon monoxide for bringing the extant molar excess of said carbon monoxide to approximate and optionally match said target molar excess.

3. The process according to claim 1, wherein the amine compound comprises diaminodiphenylmethane.

4. The process according to claim 1, wherein the colour of the isocyanate have a CIE colour grade/value L* larger than 30.

5. The process according to claim 1, wherein said isocyanate comprises 30 to 150 ppm of bromine in bound form.

6. A process for manufacturing isocyanates from an amine compound, the process comprising the steps of
   a) providing chlorine, wherein the chlorine comprises bromine in the range of 50 to 500 ppm in molecular or bound form;
   b) providing carbon monoxide;
   c) reacting said chlorine and said carbon monoxide for providing phosgene, the carbon monoxide being provided in an adjustable molar excess, wherein the mol ratio of carbon monoxide over chlorine is in a range of above 1.0001.000 up to or equal to 1.025:1.000;
   d) providing an amine compound and phosgenating said amine compound using said phosgene thereby providing said isocyanate; and
   wherein the process further comprises adjusting said adjustable molar excess for adjusting the colour of the isocyanate, wherein adjusting said molar excess comprises;
   defining a target molar excess of said carbon monoxide based upon a required colour of the isocyanate to be obtained; and
   controlling and adjusting the provision of chlorine and carbon monoxide for bringing the extant molar excess of said carbon monoxide to approximate and optionally match said target molar excess.

7. The process according to claim 6, wherein the amine compound comprises diaminodiphenylmethane.

8. The process according to claim 6, wherein the colour of the isocyanate have a CIE colour grade/value L* larger than 30.

9. The process according to claim 6, wherein said isocyanate comprises 30 to 150 ppm of bromine in bound form.

* * * * *